United States Patent

Brian et al.

[11] Patent Number: 5,844,000
[45] Date of Patent: Dec. 1, 1998

[54] PROPENONE OXIME ETHERS AND PHARMACEUTICAL COMPOSITIONS CONTAINING THEM

[75] Inventors: William Brian, Collegeville; Brian Folk, West Chester; Juan Shi, Collegeville, all of Pa.; Gerard Fabre, Prades Le Lez; Claude Tronquet, Montpellier, both of France

[73] Assignee: Sanofi, Paris Cedex, France

[21] Appl. No.: 873,540

[22] Filed: Jun. 12, 1997

[51] Int. Cl.$^6$ .......................... A01N 31/35; A01N 31/15; A01N 31/10; A01N 31/70

[52] U.S. Cl. .................. 514/633; 514/25; 514/42; 514/459; 514/518; 514/822; 536/17.1; 536/17.5; 536/29.1; 536/29.13; 549/414; 549/417; 558/37; 564/254

[58] Field of Search ............... 536/17.1, 17.5, 536/29.1, 29.13; 549/415, 417; 558/37; 564/254; 514/25, 42, 459, 518, 633, 822

[56] References Cited

U.S. PATENT DOCUMENTS

| | | | |
|---|---|---|---|
| 4,331,680 | 5/1982 | Giles et al. | 558/37 |
| 5,166,416 | 11/1992 | Congy et al. | 549/59 |
| 5,290,951 | 3/1994 | Congy et al. | 549/59 |

*Primary Examiner*—Peter O'Sullivan
*Attorney, Agent, or Firm*—Mary P. Bauman; Michael D. Alexander

[57] ABSTRACT

This invention relates to novel propenone oxime ethers, methods of preparing them and pharmaceutical compositions containing them. The compounds have the formula:

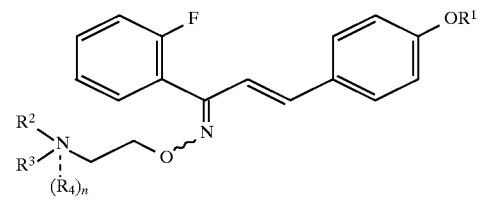

wherein $R^1$ is H, or glucuronide;

$R^2$ and $R^3$ are independently H or methyl;

$R^4$ is 0, or glucuronide, and n is 0 or 1, provided that when $R^1$ is H, n is 1.

3 Claims, No Drawings

PROPENONE OXIME ETHERS AND PHARMACEUTICAL COMPOSITIONS CONTAINING THEM

BACKGROUND OF THE INVENTION

Congy et al., U.S. Pat. No. 5,166,416 discloses propenone oxime ethers that are antagonists of the $5HT_2$ receptors. Examples 11, 12 and 23–28 therein describe various salts of SR 46349 having the structure:

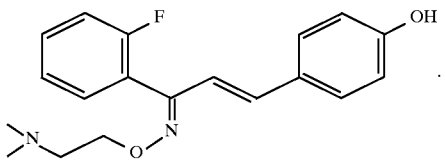

SUMMARY OF THE INVENTION

We have discovered that SR 46349 is metabolized to a variety of different analogs, including various propenone oxime ethers via a number of different pathways including N-oxidation, N-demethylation, glucuronidation and sulfation.

It is an advantageous feature of this invention that analogs of SR 46349 are provided which find utility in pharmaceutical compositions having a high affinity for the $5HT_2$ receptor.

It is another advantageous feature of this invention that analogs of SR 46349 are provided which find particular utility as pro-drugs in pharmaceutical compositions.

DESCRIPTION OF THE PREFERRED EMBODIMENTS

Trans 1-N,N-dimethylaminoethoxyimino 1-(2-fluorophenyl)-3-(4-hydroxyphenyl) 2-propene hemifumarate, also known as trans-4-[(3A) 3-((dimethylaminoethyl)oxyimino)-3-(2-fluorophenyl propen-1-yl] phenol hemifumarate or SR 46349B is a potent $5-HT_2$ antagonist which is being clinically investigated for the treatment of depression. This particular salt of SR 46349 is described by Congy et al., U.S. Pat. No. 5,166,416, Example 12.

According to this invention, there are provided compounds having the formula:

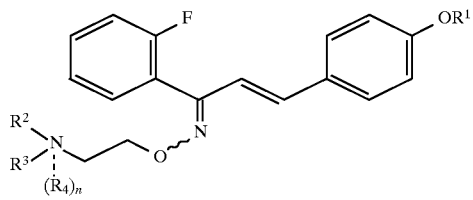

In the structural formula above,
  $R^1$ is H, glucuronide or sulfate;
  $R^2$ and $R^3$ are independently H or methyl;
  $R^4$ is O, or glucuronide; and
  n is 0 or 1;
provided that when $R^1$ is H, n is 1.
When $R_4$ is O, the compound is in the form of an N-oxide.

As shown below, most of the compounds of this invention have been identified as mixtures in various proportions of syn and anti-isomers as described by Congy et al. in U.S. Pat. No. 5,166,416 cited above.

As used herein, glucuronide, also known as glucuronoside, is intended to refer to a compound in which glucuronic acid, combined as a sugar (hexose), not as an acid, is linked by a glycosidic bond to a group e.g., a hydroxyl or carboxyl group, on another compound.

The N-oxide, sulfate and glucuronide compounds described herein can be prepared by conventional organic chemistry synthetic techniques. Alternatively, the N-oxide, sulfate and glucuronide compounds can be enzymatically synthesized using appropriate enzyme systems, for example, containing the cofactors phosphoadenosinephosphosulfate or UDP-glucuronic acid. The compounds of this invention can also be isolated from mammalian samples of plasma, urine and/or feces after dosing with SR 46349. SR 46349 can be prepared as described by Congy et al., U.S. Pat. No. 5,166,416, the disclosure of which is hereby incorporated by reference in it entirety.

The compounds are generally administered in unit doses. The unit doses are preferably formulated in pharmaceutical compositions in which the active principle is mixed with a pharmaceutical excipient.

According to another aspect, the invention relates to pharmaceutical compositions in which the active principle is an aforementioned compound or a pharmaceutically acceptable salt thereof.

In the pharmaceutical compositions according to the invention for oral, sublingual, subcutaneous, intramuscular, intravenous, transdermic, local or rectal administration, the active ingredients can be administered in unit forms of administration, mixed with conventional pharmaceutical excipients, to animals and to man. The suitable unit forms of administration comprise oral forms such as tablets, capsules, powders, granules and oral solutions or suspensions, sublingual and buccal forms of administration, subcutaneous, intramuscular, intravenous, intranasal or intraoccular forms of administration and rectal forms of administration.

Each unit dose can contain 0.1 to 500 mg of active ingredient, preferably 2.5 to 125 mg, in combination with a pharmaceutical excipient. Each unit dose can be administered 1 to 4 times per day.

When a solid composition is prepared in tablet form, the main active ingredient is mixed with a pharmaceutical excipient such as gelatine, starch, lactose, magnesium stearate, talc, gum arabic or the like. The tablets can be coated with saccharose or suitable other substances or treated so that they have prolonged or delayed activity and so that they continuously release a given quantity of the active principle.

A preparation in capsules is obtained by mixing the active ingredient with a diluent and pouring the resulting mixture into soft or hard capsules.

A preparation in syrup or elixir form can contain the active ingredient together with a sweetener, preferably without calories, and methyl paraben and propyl paraben antiseptics and suitable flavouring and dye.

The powders or granules dispersible in water can contain the active ingredient mixed with dispersing agents or wetting agents or suspension agents such as polyvinylpyrrolidone, and with sweeteners or taste adjusters.

Rectal administration is made via suppositories prepared with binders such as cocoa butter or polyethylene glycols, which melt at the rectal temperature.

Parenteral, intranasal or intraocular administration is via aqueous suspensions, or isotonic saline solutions or sterile injectable solutions containing pharmacologically compatible dispersing and/or wetting agents, e.g. propylene glycol or butylene glycol.

Alternatively the active principle can be formulated in microcapsules, with one or more excipients or additives if required.

The compounds have low toxicity. More particularly their acute toxicity is compatible with use thereof as drugs, e.g. to prevent clotting of platelets, or as psychotropic drugs.

For this purpose, mammals requiring this treatment are given an effective quantity of the compound or of one of its pharmaceutically acceptable salts.

The aforementioned compounds and their pharmaceutically acceptable salts can be used in daily doses of 0.01 to 10 mg per kilogram body weight of the mammal under treatment, preferably at daily doses of 0.1 to 5 mg/kg. In man, the dose can preferably vary from 0.5 to 500 mg per day, more particularly from 2.5 to 250 mg depending on the patient's age or the type of treatment, i.e. whether prophylactic or curative.

The following examples illustrate the invention.

The objective of this study was to quantitate the biotransformation of $^{14}$C-SR 46349B in humans. Six healthy male volunteers were treated orally with a single 30 mg dose of $^{14}$C-SR 46349B (corresponding to 35.4 mg of the salified compound), labeled on the C-1 position of the propenyl chain with $^{14}$C (1.375 MBq). Excretion-balance, plasma and blood pharmacokinetics of radioactivity, and clinical safety/tolerance were reported. Plasma, urine and fecal homogenates were analyzed for quantitation and identification of SR 46349B and metabolites.

EXPERIMENTAL PROCEDURE

Reagents for Metabolites Identification and Quantitation

Scintillation cocktails (Biofluor, Ultima, M, Carbo-sorb and Permafluor E+), combustocones and pads were purchased from Packard Instrument Company (Meriden, Conn.). Bond-Elut solid phase extraction cartridges (3 mL) were purchased from Varian (Harbor City, Calif.). HPLC columns were purchased from YMC, Inc. (Wilmington, N.C.). All other reagents and solvents used in this study were of standard reagent grade or better.

TEST ARTICLE

Formulation

[1-Propenyl-$^{14}$C]-SR 46349B was synthesized by Sanofi in Alnwick, UK, using a process similar to that described in U.S. Pat. No. 5,166,416. Radiochemical purity of drug substance was determined to be 99%. Specific activity of drug product was determined to be 1.2375 $\mu$Ci/mg. $^{14}$C-SR 46349B was administered in a single gelatin capsule.

Administration

Subjects were fasted overnight prior to the morning of $^{14}$C-SR 46349B administration. All subjects received a single oral 30 mg dose of $^{14}$C-SR 46349B (corresponding to 35.4 mg of the unsalified compound) in a single gelatin capsule. The capsule was dropped directly in the mouth and swallowed with 150 mL of tap water at about 8:00 AM. Ingestion of the capsule was verified by inspection of the oral cavity of each subject.

SAMPLE COLLECTION

Plasma Samples

Blood samples were obtained at 0, 0.5, 1, 1.5, 2, 2.5, 3, 4, 6, 8, 10, 12, 16, 24, 36, 48, 72, 96, 120, 144, 168, 192, 216, 240, 264, 288 and 312 hr after dosing. For each sample, approximately 7 mL of blood (22 mL at 2, 3, 4, 8, 12, 24 and 48 hrs after dosing) was drawn into polypropylene collection tubes containing lithium heparin (as an anticoagulant). Following the removal of 1 mL of blood for radiocarbon analysis, samples were centrifuged (within 30 min) at 2000–3000×g for 10 min and the plasma transferred into polypropylene transport tubes. All samples were stored frozen ($\leq-18°$ C.) until analysis.

Urine Samples

All voided urine was collected in polypropylene bottles and stored refrigerated (2°–8° C.) until the collection interval was completed. Collection intervals were 0 (pre-dose), 0–12, 12–24, 24–28, 48–72, 72–96, 96–120, 120–144, 144–168, 168–192, 192–216, 216–240, 240–264, 264–288, 288–312 and 312–336 hr after dosing. The samples were weighed and mixed at the end of each collection interval and a 25 mL aliquot from each collection interval was transferred into polypropylene vials. All samples were stored frozen ($\leq-18°$ C.) until analysis.

Fecal Samples

All stools were collected in polypropylene bags, sealed and immediately frozen ($\leq-18°$ C.). The last stool was obtained at least 276 hr after dosing. All stools within a 24 hr period were combined for analysis, mixed with distilled water (enough to produce a fluid consistency after homogenizatoin, approximately 80% (w/v) typically) and the mixture was homogenized for approximately 120 seconds in a stomacher. Following homogenization, a 25 mL aliquot from each collection interval was transferred into transport tubes. All samples were stored frozen ($\leq-18°$ C.) until analysis.

ASSAY METHODOLOGIES

Plasma Concentrations of SR 46349

The concentration of SR 46349 in plasma samples was determined using a validated HPLC method with UV detection at 320 nm. Briefly, the procedure involved adding 1 mL of plasma to 0.05 mL of a 10 mg/L solution of internal standard, followed by vortex mixing. After storing in the dark for approximately 15 min, 2.0 mL of titrisol buffer (pH 10) was added and samples were immediately applied to Extrelut 3 columns. After approximately 15 minutes in the dark, columns were eluted with 14 mL of methylene chloride. The samples were dried at room temperature and resuspended in 0.15 mL of mobile phase and 0.05 mL was analyzed. The HPLC system utilized a Hewlett-Packard Model 1050 HPLC system and a Lichrospher 100-RP18 (4.0×125 mm; 5$\mu$) column with a solvent system of TEA buffer (pH 3.7): acetonitrile (77:23, v/v) at a flow rate of 1.2 mL/min.

Unknown concentrations of SR 46349 were quantified by reference to a $1/y^2$ weighted regression analysis of the peak-area ratio (SR 46349/internal standard) versus concentration of the calibration curve standards. The LOQ of SR 46349 in plasma was 0.0025 mg/L.

Plasma, Urine and Fecal Concentrations of Radioactivity

Aliquots of plasma and urine samples were added directly to Ready-Safe scintillant (9 mL), hand shaken for a few seconds and left for at least 2 hours prior to counting. Aliquots of fecal homogenates were weighed in a Combusto-Cone fitted with a CombustoPad. The samples were allowed to dry overnight before combustion in a Packard Sample Oxidizer, Model 307 (Meriden, Conn.). Carbo-Sorb and Permafluor E$^+$were used as scintillants (10 mL). Samples mixed with scintillant were left for at least 4 hours prior to counting. Radioactivity assays were performed with a Packard Instruments Tri-Carb, Model 1600TR Liquid Scintillation System. The LOQ was set at 12 cpm above background.

Pharmacokinetic Parameter Analysis for SR 46349

Model-independent pharmacokinetic parameters for plasma concentrations of SR 46349 were calculated for each subject. The maximum observed plasma concentration ($C_{max}$) of SR 46349 and its corresponding time ($t_{max}$) were determined by visual inspection of individual concentration-time profiles. Half-life (t ½) was calculated from the ratio of $\ln(2)/\lambda_Z$, where $\lambda_Z$ is the regressed slope of the terminal phase. The area under the plasma concentration of SR 46349-versus-time-curves ($AUC_{(0-t)}$) was calculated using the trapezoidal rule. AUC was calculated for the sum of $AUC_{(0-t)}$ and $Cp(1)/\lambda_Z$ wherein $Cp(1)$ is the last measurable concentration time point. Nominal sample times were used to calculate pharmacokinetic parameters.

METABOLISM

Determinations of Metabolite Profiles

Quantitation of Urinary Metabolites

A representative pool of urine was prepared for each subject by mixing aliquots from each collection interval in proportion to the percent of radioactivity present in each collection interval. Pools were prepared to represent approximately 95% of total collected urinary radioactivity.

Aliquots of pooled urine samples (1 mL) were applied to 3 mL Bond-Elut solid-phase extraction cartridges (pre-conditioned with 2 mL of methanol followed by 2 mL of water), washed with 2 mL of water followed with 2 mL of methanol:water (1:4 v/v), and then eluted with 3 mL of methanol. Eluates were dried under nitrogen using a TurboVap evaporator at 40° C. Dried samples were reconstituted in 0.25 mL of 20 mM aqueous ammonium acetate (pH 3.0): acetonitrile (9:1, v/v) by vigorous mixing and sonication for 5 min and then 0.18 mL was injected onto the HPLC. Pools for each subject were extracted and analyzed in triplicate.

Quantitation of Fecal Metabolites

A representative pool of fecal homogenate was prepared for each subject by mixing aliquots from each collection interval in proportion to the percent of radioactivity present in each collection interval. Pools were prepared to represent approximately 95% of total collected fecal radioactivity.

Aliquots of pooled fecal homogenates (approximately 3 grams) were mixed with 6 mL of methanol in 15 mL polypropylene centrifuge tubes for 3 minutes on a multi-tube vortexer, and then centrifuged (4500×g×10 min). The pellets were extracted twice more with 5 mL of methanol and supernatants from the three extraction were combined and dried under nitrogen for approximately 15 hr using a TurboVap evaporator at 35° C.

Dried samples were reconstituted in 0.75 mL of methanol:water (3:1, v/v) with vigorous mixing and sonication for 10 min, followed by centrifugation (15000 g×5 min). The supernatant was concentrated under nitrogen at 40° C. using a TurboVap evaporator for approximately 30 min. The concentrated supernatants were diluted to approximately 0.5 mL (final volume of the diluted solution was measured with an Eppendorf pipetman) with methanol:water (1:1, v/v), and then 0.18 mL was injected onto the HPLC. Pools for each subject were extracted and analyzed in triplicate, as described below.

Quantitation of Plasma Metabolites

Pools of plasma for each collection time were prepared by mixing equal amounts of plasma from all subjects. This made available enough plasma at each time point to quantitate metabolites. Aliquots of plasma pools (1 mL) were applied to 3 mL Bond-Elut solid phase extraction cartridges (pre-conditioned with 2 mL of methanol followed by 2 mL of water), washed with 2 mL of water and eluted with 3 mL of ethanol. Eluates were concentrated under nitrogen using a TurboVap evaporator at 40° C. until approximately 0.3 mL of solution remained. Due to low amounts of radioactivity in plasma, five concentrated extracts from the same time point were combined. Tubes that contained extract were rinsed twice with 0.2 mL of methanol and rinses combined with the extract. Samples were dried under nitrogen at 40° C. using a TurboVap evaporator. Dried samples were reconstituted in 0.25 mL of 20 mM aqueous ammonium acetate (pH 3.00) :acetonitrile (9:1, v/v) by vigorous mixing and sonication for 5 min. After centrifugation (4500 g×5 min), 0.18 mL of supernatant was injected onto the HPLC. Pools for each collection time were analyzed in triplicate.

Chromatographic Methods

Metabolite quantitation was conducted with an HP1090 HPLC system (Hewlett Packard, Wilmington, Del. HPLC eluant was fraction collected (0.33 mL/fraction using a FOXY™ Model 200 fraction collector; Isco, Lincoln, Nebr.). Fractions were mixed with 5 mL of Biofluor cocktail and then counted using a Tri-Carb 2700TR liquid scintillation counter (Packard, Meriden, Conn.).

Prior to profiling urine, fecal or plasma extract, a urine pool extract was chromatographed as a reference standard to determine that the HPLC system was working properly and to compare retention times of metabolites in feces and plasma to urine. HPLC eluant for the urine reference standard was directed through a Packard Radiomatic 500TR Flowone/Beta radioactivity detector. Eluant was mixed with Ultima M scintillation cocktail using a 1:3 mixture (eluant:cocktail).

Calculation of Metabolite Concentrations and Excretion

Sample extraction and HPLC column recoveries were calculated using measured radioactivity in samples, sample extracts and HPLC eluants. Recoveries of 100% were based on the expected amount of radioactivity in a sample prior to extraction or HPLC analysis.

Urinary and fecal metabolites are expressed as a percentage of the radioactivity in each matrix and as a percentage of excreted (recovered) radioactivity. Values were corrected for total experimental recoveries.

METABOLITE STRUCTURAL ELUCIDATION

Characterization of Urine and Fecal Metabolites

Urine samples were prepared by pooling equal volumes across subjects from the 0–48 hr collection intervals. Aliquots of pooled urine samples (1 mL) were applied to 3 mL Bond-Elut solid-phase extraction cartridges (pre-conditioned with 2 mL of methanol followed by 2 mL of water), washed with 2 mL of water and 2 mL of methanol :water (1:4, v/v), and then eluted with 3 mL of methanol. Eluates were dried under nitrogen at 40° C. using a TurboVap evaporator. Dried samples were reconstituted in 0.25 mL of 20 mM aqueous ammonium acetate (pH 3.0) :acetonitrile (9:1, v/v) by vigorous mixing and sonication for 5 min and analyzed by LC-MS/MS. Sometimes extracts were pooled after reconstitution to increase the amount of material available for analysis.

Fecal homogenate samples were prepared and extracted as described above.

Liquid Chromatography-mass Spectrometry

LC-MS/MS was performed using a Hewlett-Packard HP1090 HPLC system interfaced with a Finnigan MAT TSQ 7000 (Finnigan MAT, San Jose, Calif.). The mass spectrometer was optimized in the positive ion, electrospray (ESI) mode using an unlabeled SR 46349B standard. Source parameters were optimized using the HPLC with approximately 40% of the column eluant directed to the ESI source. The remaining eluant was split to a fraction collector. The parent molecular ion (m/z 329) was scanned in the selected ion monitoring (SIM) mode for source optimization. The collision energy and collision gas pressure were optimized by scanning MS/MS product ions of m/z 329.

Radiochromatograms of pooled samples were generated from fractions obtained from the HPLC system used for metabolite quantitation or after splitting the eluant for LC-MS/MS analysis. These chromatograms were compared to confirm that the retention times of SR 46349 and metabolites on the system used for LC-MS/MS analysis corresponded to those obtained on the system used for metabolite quantitation.

RESULTS
Pharmacokinetic Results

Plasma Concentration of SR 46349 and Radioactivity

Following oral administration of $^{14}$C-SR 46349B, plasma concentrations of SR 46349 reached a mean (±SD) $C_{max}$ of 0.05 (±0.01) mg/L between 1.5 and 4 hours after dosing. After this time, the concentrations declined rapidly with a terminal elimination half-life of 22.9 (±7.3) hr. The mean (±SD) AUC was 1.2 (±0.15) mg●hr/L.

Maximal plasma concentrations of radioactivity were higher than those observed for intact drug, reaching a mean (±SD) $C_{max}$ of 0.16 (±0.02) mg eq/L between 2 and 12 hours after dosing. The terminal elimination half-life for plasma radioactivity was 63.3 (±5.6) hr. The mean (±SD) AUC was 13.7 (±2.1) mg eq●hr/L, approximately 11 times greater than the mean plasma AUC for SR 46349.

BIOTRANSFORMATION
Metabolite Profiling

Urinary Metabolites

The cumulative urinary excretion of radioactivity up to 336 hr post-dose represented 70.3 (±4.6)% (mean (±SD), range 63.1 to 77.1%) of the administered does. Extraction recovery for urine was 95.4 (±4.8)%. Column recovery for urine extracts was 102.5 (±6.0)%. The peak labeled HU17 had a similar retention time with SR 46349. Twenty-four metabolites were evident by radiochromatography or LC-MS/MS in extracted urine samples. Approximately 82% of excreted urinary radioactivity was accounted for by SR 46349 and metabolites. Of the 24 metabolites noted in urine, 17 have been structurally characterized using LC-MS/MS. Also, based on HPLC retention times, metabolites HU16 and HU19 corresponded to N-demethlyated SR 46349 and the N-demethylated isomer of SR 46349.

Fecal Metabolites

The cumulative fecal excretion of radioactivity up to 276 hr post-dose represented 21.6 (±3.5)% (mean (±SD), range 16.4 to 26.5%) of the administered does. Extraction recovery for fecal homogenates was 79.6 (±1.5)%. Column recovery for fecal homogenate extracts was 103.9 (±2.8)%. The peak labeled HF17 was identified as SR 46349 based on similar HPLC retention times and mass spectral data with standard SR 46349. Nine metabolites and the isomer of SR 46349 (HF16, HF18&19, HF20&21, HF22, HF25A, HF25B and HF25C) were evident by radiochromatography or LC-MS/MS in extracted fecal samples. These metabolites corresponded to metabolites with the same identification number in urine based on HPLC retention time, and were also confirmed using LC-MS/MS (except for HF18, HF21 and HF25). It appeared that HF25 consisted of 3 compounds in feces. Metabolite H25 was a minor component of urine but represented a significant proportion (approximately 12%) of fecal radioactivity. Approximately 55% of excreted fecal radioactivity was accounted for by SR 46349 and metabolites.

Plasma Metabolites

Extraction recovery for plasma ranged from approximately 85 to 95% over the different time points investigated. Column recovery for plasma extracts ranged from approximately 103 to 120%. Radiochromatograms of plasma contained at least 16 peaks consistent with metabolites identified in urine. Plasma metabolites were identified by comparison of HPLC retention times with urinary metabolites, using chromatograms obtained on the same day and by LC-MS/MS. The plasma concentrations of SR 46349B (HP17) were higher than any single metabolite, except at the 48 hr time point.

METABOLITE IDENTIFICATION
Identification of Urinary Metabolites

Experimental results for identification of SR 46349 are presented first, followed by results for oxidative metabolites, and then conjugated metabolites.

Mass Spectral Characterization of an Authentic SR 46349B Standard

The positive full scan electrospray spectrum of an authentic standard of SR 46349B showed a base peak at m/z 329 ([MH]$^+$) indicating a molecular weight of 328. The product ion spectrum of the m/z 329 ion contained several characteristic fragment ions for this compound. The major fragment produced was at m/z 240, corresponding to cleavage of the N—O bond of the oxime. The 240 fragment contained both substituted phenyl rings connected by the $C_3H_2N$. The 240 fragment underwent further fragmentation and produced characteristic ions at 119 (phenol+HC=CH), 144 (240–$FC_6H_4$), and 91 (tropylium ion). The remaining $(CH_3)_2NCH_2CH_2O$ fragment produced characteristic ions at m/z 44, 58 and 72. The characteristic ions described were used to identify potential metabolites and to assist in determining sites of metabolism.

Identification of SR 46349 (HU17) and its Isomer, HU20

The positive full scan electrospray spectrum of urine component HU17 showed a base peak at m/z 329 ([MH]$^+$) indicating a molecular weight of 328. The product ion spectrum of the m/z 329 ion contained several characteristic ions of the parent drug. The major fragment produced was at m/z 240, corresponding to cleavage of the N—O bond of the oxime. The 240 fragment contained both substituted phenyl rings connected by the $C_3H_2N$. The 240 fragment underwent further fragmentation and produced characteristic ions at 119 (phenol+HC=CH), 144 (240 -$FC_6H_4$), and 91 (tropylium ion). The remaining $(CH_3)_2NCH_2CH_2O$ fragment was evident at m/z 88. The tertiary amine fragmented further and produced characteristic ions at m/z 44, 58, and 72. These data, combined with evidence of similar retention time with an authentic SR 46349 standard, indicated that HU17 was the parent drug. Similar data were obtained for HU20 and indicated that HU20 was an isomer of HU17. Corresponding components were identified in human fecal samples and were designated HF17 and HF20.

Identification of HU22 and its Isomer. HU23

The positive full scan electrospray spectrum of urine metabolite HU22 showed a base peak at m/z 345 ([MH]$^+$) indicating a molecular weight of 344. This molecular weight corresponded to an addition of 16 amu and suggested an oxidation of SR 46349. The product ion spectrum of the m/z 345 ion contained characteristic ions of the parent drug. The major fragment produced was at m/z 240, corresponding to cleavage of the N—O bond of the oxime. The 240 fragment contained both substituted phenyl rings connected by the $C_3H_2N$. The 240 fragment underwent further fragmentation and produced characteristic ions at 119 (phenol +HC=CH), 144 (240 - $FC_6H_4$), and 91 (tropylium ion). The remaining $(CH_3)_2NCH_2CH_2O$ fragment was evident at m/z 88. An additional mass peak was observed at m/z 106 and corresponded to the oxidation of alkylamine moiety. Although this represented an addition of 18 amu to this fragment, the mechanism for the formation of the m/z 88 fragment has an inherent loss of two protons. This mechanism was altered by the presence of the oxide and accounted for the two additional protons observed. This oxidized tertiary amine fragmented further and produced characteristic ions at m/z 44, 58, and 72. These data, combined with evidence of similar HPLC retention time and mass spectral data, indicated that HU22 was the N-oxide of SR 46349. Similar data were obtained for HU23 and indicated that HU23 was an isomer of HU22. Corresponding metabolites were identified in human fecal samples and were designated HF22 and HF23.

Identification of Metabolite HU2 and its Isomer, HU3

The positive full scan electrospray spectrum of urine metabolite HU2 showed a base peak at m/z 505 ([MH]$^+$) indicating a molecular weight of 504. This molecular weight corresponded to an addition of 176 amu and suggested glucuronidation of SR 46349. The product ion spectrum of the m/z 505 ion contained characteristic ions of the parent drug. The major fragment produced was at m/z 240, corresponding to cleavage of the N—O bond of the oxime and the loss of 176 amu. The 240 fragment contained both substituted phenyl rings connected by the $C_3H_2N$. The 240 fragment underwent further fragmentation and produced the characteristic ions at 119 (phenol+HC=CH). The fragment at m/z 329 corresponded to the parent drug and resulted from the facile loss of 176 amu from the metabolite molecular ion. The fragment at 416 corresponded to the loss of $(CH_3)_2NCH_2CH_2O$ resulting from cleavage of the oxime and indicated that conjugation occurred on the m/z 240 fragment. The most likely site of conjugation was on the phenolic oxygen. The $(CH_3)_2NCH_2CH_2O$ fragment produced characteristic ions at m/z 58 and 72. These data indicated that HU2 was the phenolic glucuronide of the parent drug. Similar data were obtained for HU3 and indicated that HU3 was an isomer of HU2.

Identification of Metabolite HU4 and its Isomer, HU6

The positive full scan electrospray spectrum of urine metabolite HU4 showed a base peak at m/z 521 ([MH]$^+$) indicating a molecular weight of 520. This molecular weight corresponded to an addition of 192 amu and suggested an oxidation and glucuronidation of SR 46349. The product ion spectrum of the m/z 521 ion contained characteristic ions of the parent drug. The major fragment produced was at m/z 240, corresponding to cleavage of the N—O bond of the oxime and the loss of 192 amu. The 240 fragment contained both substituted phenyl rings connected by the $C_3H_2N$. The fragment at m/z 345 corresponded to the addition of 16 amu to the parent drug and resulted from the facile loss of 176 amu from the metabolite molecular ion. The fragment at 416 corresponded to the loss of $(CH_3)_2NCH_2CH_2O$ and an additional 16 amu resulting from cleavage of the oxime and indicated that conjugation occurred on the m/z 240 fragment and oxidation occurred on the $(CH_3)_2NCH_2CH_2O$ moiety. The most likely site of conjugation was on the phenolic oxygen. The oxidated $(CH_3)_2NCH_2CH_2O$ fragment produced characteristic ions at m/z 58, 72, 88 and 106. These data indicated that HU4 was the phenolic glucuronide of the N-oxide of the parent drug. Similar data were obtained for HU6 and indicated that HU6 was an isomer of HU4.

Identification of Metabolite HU1

The positive full scan electrospray spectrum of urine metabolite HU1 showed a base peak at m/z 491 ([MH]$^+$) indicating a molecular weight of 490. This molecular weight corresponded to an addition of 162 amu and suggested a glucuronidation and demethylation of SR 46349. The product ion spectrum of the m/z 491 ion contained characteristic ions of the parent drug. The major fragment produced was at m/z 240, corresponding to cleavage of the N—O bond of the oxime and the loss of 176 amu. The 240 fragment contained both substituted phenyl rings connected by the $C_3H_2N$. The fragment at m/z 315 corresponded to the loss of 14 amu to the parent drug and resulted from the facile loss of 176 amu from the metabolite molecular ion. The fragment at 416 corresponded to the loss of the alkylamine moiety resulting from cleavage of the oxime. This indicated that conjugation occurred on the m/z 240 fragment and demethylation occurred on the $(CH_3)_2NCH_2CH_2O$ moiety of the parent drug. The most likely site of conjugation was on the phenolic oxygen. The alkylamine fragment produced characteristic ions at m/z 44 and 58. These data indicated that HU1 was the phenolic glucuronide of N-demethylated SR 46349. It was likely that the corresponding isomer of HU1 co-eluted under the chromatographic conditions used.

Identification of Metabolite HU9 and its Isomer, HU14

The positive full scan electrospray spectrum of urine metabolite HU9 showed a base peak at m/z 409 ([MH]$^+$) indicating a molecular weight of 408. This molecular weight corresponded to an addition of 80 amu and suggested sulfation of SR 46349. The product ion spectrum of the m/z 409 ion contained characteristic ions of the parent drug. The major fragment produced was at m/z 240, corresponding to cleavage of the N—O bond of the oxime and the loss of 80 amu. The 240 fragment contained both substituted phenyl rings connected by the $C_3H_2N$. The 240 fragment underwent further fragmentation and produced the characteristic ions at 119 (phenol+HC=CH) and 144 (240 - $FC_6H_4$). The fragment at m/z 329 corresponded to the parent drug and resulted from the facile loss of 80 amu from the metabolite molecular ion. The fragment at 320 corresponded to the loss of the $(CH_3)_2NCH_2CH_2O$ resulting from cleavage of the oxime and indicated that conjugation occurred on the m/z 240 fragment. The most likely site of conjugation was on the phenolic oxygen. The $(CH_3)_2NCH_2CH_2O$ fragment produced characteristic ions at m/z 58, 72 and 88. These data indicated that HU9 was the phenolic sulfate conjugate of the parent drug. Similar data were obtained for HU14 and indicated that HU14 was an isomer of HU9.

Identification of Metabolite HU12 and its Isomer, HU15

The positive full scan electrospray spectrum of urine metabolite HU12 showed a base peak at m/z 425 ([MH]$^+$) indicating a molecular weight of 424. This molecular weight corresponded to an addition of 96 amu and suggested an oxidation and sulfation of SR 46349. The product ion spectrum of the m/z 425 ion contained characteristic ions of the parent drug. The major fragment produced was at m/z 240, corresponding to cleavage of the N—O bond of the oxime and the loss of 96 amu. The 240 fragment contained both substituted phenyl rings connected by the $C_3H_2N$. The fragment at m/z 345 corresponded to the addition of 16 amu to the parent drug and resulted from the facile loss of 80 amu from the metabolite molecular ion. The fragment at 320 corresponded to the loss of $(CH_3)_2NCH_2CH_2O$ and an additional 16 amu resulting from cleavage of the oxime and indicated that conjugation occurred on the m/z 240 fragment and oxidation occurred on the $(CH_3)_2NCH_2CH_2O$ moiety. The most likely site of conjugation was on the phenolic oxygen. The oxidized $(CH_3)_2NCH_2CH_2O$ fragment produced characteristic ions at m/z 58, 72, 88 and 106. These data indicated that HU12 was the phenolic sulfate of the N-oxide of the parent drug. Similar data were obtained for HU15 and indicated that HU15 was an isomer of HU12.

Identification of Metabolite HU8 and its Isomer, HU13

The positive full scan electrospray spectrum of urine metabolite HU8 showed a base peak at m/z 395 ([MH]$^+$)

indicating a molecular weight of 394. This molecular weight corresponded to an addition of 66 amu and suggested a sulfation and demethylation of SR 46349. The product ion spectrum of the m/z 425 ion contained characteristic ions of the parent drug. The major fragment produced was at m/z 240, corresponding to cleavage of the N—O bond of the oxime and the loss of 80 amu. The 240 fragment contained both substituted phenyl rings connected by the $C_3H_2N$. The fragment at m/z 315 corresponded to the loss of 14 amu from the parent drug and resulted from the facile loss of 80 amu from the metabolite molecular ion. The fragment at 320 corresponded to the loss of the alkylamine moiety resulting from cleavage of the oxime. This indicated that conjugation occurred on the m/z 240 fragment and demethylation occurred on the $(CH_3)_2NCH_2CH_2O$ moiety of the parent drug. The most likely site of conjugation was on the phenolic oxygen. The alkylamine fragment produced a characteristic ion at m/z 58. These data indicated that HU8 was the phenolic sulfate conjugate of N-demethylated SR 46349. Similar data were obtained for HU13 and indicated that HU13 was an isomer of HU8.

Identification of Metabolite HU10A and its Isomer, HU10B

The positive full scan electrospray spectrum of urine metabolite HU10A showed a base peak at m/z 505 ([MH]$^+$) indicating a molecular weight of 504. This molecular weight corresponded to an addition of 176 amu and suggested a glucuronidation of SR 46349. The product ion spectrum of the m/z 505 ion contained characteristic ions of the parent drug. The major fragment produced was at m/z 329, corresponding to the facile loss of 176 amu. The characteristic fragment at m/z 240, corresponding to cleavage of the N—O bond of the oxime and the loss of 176 amu, was also produced. The 240 fragment contained both substituted phenyl rings connected by the $C_3H_2N$. The 240 fragment underwent further fragmentation and produced the characteristic ions at 119 (phenol+HC=CH). The fragment at m/z 416 corresponding to the loss of $(CH_3)_2NCH_2CH_2O$ resulting from cleavage of the oxime was not produced and indicated that conjugation did not occur on the m/z 240 fragment. The most likely site of conjugation was on the N,N-dimethylamine moiety. The $(CH_3)_2NCH_2CH_2O$ fragment produced characteristic ions at m/z 58 and 72. These data indicated that HU10A was the N-glucuronide of the parent drug. Similar data were obtained for HU10B and indicated that HU10B was an isomer of HU10A.

Metabolites HU5, HU7, HU11, HU18, HU21, HU24 and HU25

The positive full scan and precursor ion scan electrospray spectrum of urine metabolite HU5, HU7, HU11, HU18, HU21, HU24 and HU25 indicated that these peaks were potentially related to SR 46349, but limited concentrations of these metabolites prevented the acquisition of the interpretable product ion data required for positive identification. Each of these potential metabolites accounted for less than two percent of the total recorded radioactivity in urine.

DISCUSSION OF RESULTS

Following oral administration of a 30 mg dose of $^{14}$C-SR 46349B, maximal plasma concentrations of radioactivity were approximately 3 times higher than plasma concentrations of SR 46349 at similar $t_{max}$ values. After this point, plasma concentrations of SR46349 decline with a mean half-life of approximately 23 hr. In contrast, plasma concentrations of radioactivity decline slower with a mean terminal half-life of approximately 63 hr. The mean (±SD) AUC for plasma radioactivity was 13.7 (±2. 1) mg eq●hr/L, approximately 11 times greater than the mean plasma AUC for SR 46349 (1.20 (±0.15) mg eq●hr/L).

Of the recovered radioactivity, approximately 82% in urine and 56% in feces was accounted for as SR 46349 and metabolites. In total, approximately 76% of the excreted radioactivity was characterized radiochromatographically. The remainder of the recovered radioactivity was attributable to extraction losses (primarily feces) or non-distinct chromatography (too diffuse or too minor to characterize or identify). SR 46349 accounted for approximately 6% of the excreted radioactivity, indicating that the compound was extensively metabolized.

Altogether, 26 putative metabolites were noted in urine or feces. Structural information was obtained on 17 of these metabolites. Pathways of SR 46349 metabolism included N-oxidation, N-demethylation, sulfation and glucuronidation. Some metabolites were identified that had undergone two steps of metabolism (i.e., N-oxidation or N-demethylation, followed by conjugation). For almost all the metabolites studied, two isomers were observed. Isomerization of SR 46349 has been noted previously. Therefore, it is likely that the different metabolite isomers observed were the Z and E forms, although other possible isomers can be postulated.

On a percentage basis, the N-oxide metabolite of SR 46349 (H22 & H23) accounted for the greatest percentage of excreted radioactivity (approximately 23% of excreted radioactivity), followed by the N-demethylated metabolite (H16 & H19, approximately 11% of excreted radioactivity). Furthermore, additional amounts of conjugated (sulfate and glucuronide) N-oxide and N-demethylated metabolites were noted. Collectively, these two pathways of metabolism accounted for nearly half of the excreted radioactivity. In addition to oxidative metabolites or conjugates of oxidative metabolites of SR 46349, SR 46349 was also conjugated directly with sulfate or glucuronic acid. Sulfate conjugates were phenolic, while both N-glucuronides and O-glucuronides were observed. Taken together, it appears that oxidation of SR 46349 (N-oxidation and N-demethylation) appears to be the major mechanism of metabolic clearance, with conjugation playing a lesser role.

Many of the excreted metabolites were also observed in plasma. Assignment of structures for plasma metabolites was done by comparing HPLC retention times with urine extract and by LC-MS/MS. The larger plasma AUC and longer half-life of radioactivity, when compared with SR 46349 is related to the presence of these circulating metabolites. Those metabolites which represent most of the plasma radioactivity include the N-oxide and N-demethylated phenolic sulfates of SR 46349, the phenolic sulfate of SR 46349 and the N-oxide of SR 46349. However, at all but the last time point (48 hr) plasma concentrations of SR 46349 were always higher than any individual metabolite.

It should be understood by those skilled in the art that, while the invention has been described and illustrated above in connection with certain specific embodiments, many variations and modifications may be employed without departing from the scope of the invention.

What is claimed is:

1. A compound having the formula:

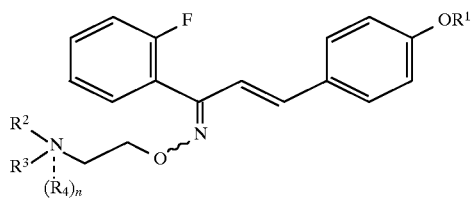

wherein $R^1$ is H, glucuronide or sulfate;

$R^2$ and $R^3$ are independently H or methyl;

$R^4$ is 0, or glucuronide, and n is 0 or 1, provided that when R is H, n is 1.

2. A pharmaceutical composition comprising an effective amount of the compound of claim 1 with a pharmaceutically acceptable carrier.

3. A method of treating depression in a mammal comprising administering to said mammal the pharmaceutical compositions of claim 2.

* * * * *